US009205145B2

(12) United States Patent
Duran

(10) Patent No.: US 9,205,145 B2
(45) Date of Patent: Dec. 8, 2015

(54) BLUETONGUE VIRUS VACCINE AND IMMUNOGENIC COMPOSITIONS, METHODS OF USE AND METHODS OF PRODUCING SAME

(75) Inventor: Joan Plana Duran, Santa Pau (ES)

(73) Assignee: Zoetis Services LLC, Florham Park, NJ (US)

( * ) Notice: Subject to any disclaimer, the term of this patent is extended or adjusted under 35 U.S.C. 154(b) by 570 days.

(21) Appl. No.: 12/744,136

(22) PCT Filed: Nov. 21, 2008

(86) PCT No.: PCT/EP2008/065993
§ 371 (c)(1),
(2), (4) Date: Oct. 15, 2010

(87) PCT Pub. No.: WO2009/065930
PCT Pub. Date: May 28, 2009

(65) Prior Publication Data
US 2011/0027316 A1 Feb. 3, 2011

(30) Foreign Application Priority Data
Nov. 21, 2007 (EP) ..................................... 07380323

(51) Int. Cl.
*A61K 39/15* (2006.01)
*C12N 7/02* (2006.01)
*C12N 7/04* (2006.01)
*A61K 39/12* (2006.01)
*A61K 39/00* (2006.01)

(52) U.S. Cl.
CPC ................. *A61K 39/15* (2013.01); *A61K 39/12* (2013.01); *A61K 2039/5252* (2013.01); *A61K 2039/552* (2013.01); *A61K 2039/55505* (2013.01); *A61K 2039/55577* (2013.01); *C12N 2720/12134* (2013.01)

(58) Field of Classification Search
None
See application file for complete search history.

(56) References Cited

U.S. PATENT DOCUMENTS

| | | | |
|---|---|---|---|
| 4,545,987 | A | 10/1985 | Giles et al. |
| 5,057,540 | A | 10/1991 | Kensil et al. |
| 6,165,995 | A | 12/2000 | Hilgers |
| 6,610,310 | B2 | 8/2003 | Hilgers |

FOREIGN PATENT DOCUMENTS

| | | |
|---|---|---|
| EP | 0 109 942 B1 | 6/1991 |
| EP | 0 362 279 B1 | 11/1995 |
| WO | WO 96/11711 | 4/1996 |
| WO | WO 96/33739 | 10/1996 |
| WO | WO98/56145 | * 12/1998 |
| WO | WO98/56415 | * 12/1998 |
| WO | WO 98/56415 | 12/1998 |
| WO | WO 99/10008 | 3/1999 |

OTHER PUBLICATIONS

Mattion et a., Vaccine 2004 vol. 22, Issues 31-32, Oct. 22, 2004, pp. 4149-4162.*
Ramakrishnan et al. Vet Res Com 2006 vol. 30, pp. 873-880.*
Breard et al. Virus Res, 2007 vol. 125, pp. 191-197.*
Luedke, A. J. et al., 1967, American Journal of Veterinary Research, vol. 28, pp. 457-460.
Hourrigan, J. L. et al., 1975, Australian Veterinary Journal, vol. 51, pp. 170-174.
Erasmus, B. J., 1975, Australian Veterinary Journal, vol. 51, pp. 209-210.
Erasmus, B. J., 1975, Australian Veterinary Journal, vol. 51, pp. 165-170.
Du Toit, R. M., 1944, Onderstepoort Journal of Veterinary Science and Animal Industry, vol. 19, pp. 7-16.
Komarov, A. and Goldsmit, L., 1951, Refuah Veterinarith, vol. 8, pp. 96-100.
Price, D. A. and Hardy, W. T., 1954, Journal of the American Veterinary Medical Association, vol. 124, pp. 255-258.
Shope, R. E. et al., 1960, Journal of Experimental Medicine, vol. 111, pp. 155-170, plates 7-10.
Livingston, Jr., C. W. and Hardy W. T., 1964, American Journal of Veterinary Research, vol. 25, pp. 1598-1600.
Luedke, A. J. et al., 1969, American Journal of Veterinary Research, vol. 30, pp. 511-516.
McKercher, D. G. et al., 1957, American Journal of Veterinary Research, vol. 18, pp. 310-316.
Alexander, R. A., et al., 1947, Onderstepoort Journal of Veterinary Science and Animal Industry, vol. 21, pp. 231-241.
Kemeny, L. and Drehle, L. E., 1961, American Journal of Veterinary Research, vol. 22, pp. 921-925.
Sambrook, Fritsch & Maniatis, *Molecular Cloning: A Laboratory Manual*, Second Edition (1989) Dold Spring Harbor Laboratory Press, Cold Spring Harbor, New York.

(Continued)

*Primary Examiner* — Mary E Mosher
*Assistant Examiner* — Myron Hill
(74) *Attorney, Agent, or Firm* — Barbara L. Renda; E. Victor Donahue

(57) ABSTRACT

Provided are immunogenic and vaccine compositions and methods for their preparation and use, which compositions are effective in protecting against, minimizing the severity of, preventing, and/or ameliorating infection of ruminants with Bluetongue virus. Administration to an animal of at least one dose of an adjuvanted and twice inactivated Bluetongue virus composition as disclosed herein is effective in providing immunity to the animal and protection from infection with Bluetongue virus, thereby reducing the severity of and/or preventing disease caused by one or more strains or serotypes of Bluetongue virus.

5 Claims, No Drawings

(56) References Cited

OTHER PUBLICATIONS

*DNA Cloning: A Practical Approach*, vols. I and II (D.N. Glover ed. 1985).
*Oligonucleotide Synthesis* (M.J. Gait ed. 1984).
*Nucleic Acid Hybridization* (B.D. Hames & S.J. Higgins eds. (1985).
*Transcription and Translation* (B.D. Hames & Higgins, eds. (1984).
*Animal Cell Culture* (R.I. Freshney, ed. (1986).
*Immobilized Cells and Enzymes* (IRL Press, (1986).
B. Perbal, *A Practical Guide to Molecular Cloning* (1984).
F. M. Ausubel et al. (eds.), Current Protocols in Molecular Biology, John Wiley & Sons, Inc. (1994).
Hood, et al., Immunology, Second Ed., Menlo Park, CA: Benjamin/Cummings, 1984. p. 384.
Erickson, A. L. et al., 1993, Journal of Immunology, vol. 151, pp. 4189-4199.
Doe, Barbara et al., 1994, European Journal of Immunology, vol. 24, pp. 2369-2376.
Remington's Pharmeceutical Sciences, E. W. Martin.
Lacaille-Dubois, M. and Wagner H., 1996, A review of the biological and pharmacological activities of saponins, Phytomedicine, vol. 2, pp. 363-386.
Kensil, C. R., 1996, Saponins as vaccine adjuvants, Critical Reviews in Therapeutic Drug Carrier Systems, vol. 13 (1-2), pp. 1-55.
Kensil, C. R. et al., 1991, Journal of Immunology, vol. 146, pp. 431-437.
Bomford, R. et al., 1992, Vaccine, vol. 10(9), pp. 572-577.
Gizurarson, S. et al. 1994, Vaccine Research, vol. 3, pp. 23-29.
Maharaj, I. et al., 1986, Canadian Journal of Microbiology, vol. 32(5), pp. 414-420.
Chavali, S. R. and Campbell, J. B., 1987, Immunobiology, vol. 174(3), pp. 347-359.
Mcl Mowat, A., 1991, Immunology, vol. 72, pp. 317-322.
Mcl Mowat, A. and Donachie, A. M., 1991, Immunology Today, vol. 12, pp. 383-385.
Sasaki, S. et al., 1998, Journal of Virology, vol. 72(6), pp. 4931-4939.
Estrada, A. et al., 1998, Comparative Immunology Microbiology & Infectious Diseases, vol. 21(3), pp. 225-236.
Mertens, P.P. et al., 1987, Virology, vol. 161(2), pp. 438-447.
Breard, E. et al., 2007, Virus Research, vol. 125(2), pp. 191-197.
Sparger, E. E. et al., 1997 "Infection of cats by injection with DNA of feline immunodeficiency virus molecular clone," Virology, vol. 238, pp. 157-160.
Willems, L. et al., 1992, "In vivo transfection of bovine leukemia provirus into sheep," Virology, vol. 189, pp. 775-777.
Jiménez-Clavero, M. A. et al., 2006, Journal of Veterinary Diagnostic Investigation, vol. 18, pp. 7-17.
Ramakrishnan, M. A. et al., 2006, Veterinary Research Communications, vol. 30(8), pp. 873-880.
Savini, G. et al., 2007, Veterinary Microbiology, vol. 124(1-2), pp. 140-146.
PCT/EP2008/065993 International Search Report, date of mailing Apr. 27, 2009.

\* cited by examiner

BLUETONGUE VIRUS VACCINE AND IMMUNOGENIC COMPOSITIONS, METHODS OF USE AND METHODS OF PRODUCING SAME

FIELD OF THE INVENTION

The invention relates to a vaccine or immunogenic composition for immunizing ruminants against pathogenic strains or serotypes of Bluetongue Virus (BTV) and a method for making the vaccine and immunizing ruminants with these compositions.

BACKGROUND OF THE INVENTION

Bluetongue, an arthropod-borne viral disease, occurs in cattle, sheep, goats, and wild ruminants. Bluetongue lesions in affected animals resemble infectious bovine virus diarrhea, vesicular stomatitis virus, malignant catarrhal fever, mycotic stomatitis, rinderpest, photosensitization, and foot and mouth disease. Bluetongue virus (BTV) has been incriminated as a cause of hydranencephaly in cattle and of infertility, abortion, and birth of defective young in cattle and sheep. Twenty four serotypes are reported in the literature as causing problems ranging from inapparent infection to acute fulminating infection. Chronic, persistent virus shedding cattle have also been recognized. With BTV there is a marked loss of body condition and marketing of slaughter animals may be delayed. In BTV-infected sheep, wool growth may be impaired by the development of wool breaks which produce a defective or low yielding fleece. The marked debility following BTV infections may result in a lowering of resistance to secondary bacterial or chlamydial infections and other predatory factors. The reproductive efficiency of infected animals is also adversely affected.

Abortions and defective offspring are observed in infected animals, and some animals may be barren for one or more breeding seasons. The most significant damage inflicted by bluetongue infections is economic loss resulting from embargoes and stringent testing requirements imposed on producers who export cattle, cattle semen, and sheep from bluetongue endemic areas.

Under natural conditions, transmission of the virus occurs via the bites of at least four Culicoides species, e.g., sand flies, midges. The biological transmission of BTV between cattle and sheep by the same culicoid vector has been demonstrated experimentally (Luedke et al, 28 AJVR 457 (1967)). Cattle, sheep, and many species of wild ruminants may act as reservoirs of BTV producing a means for the virus to overwinter. A persistent BTV viremia, which can last as long as three years has been identified in cattle (Hourrigan, 51 Aust Vet J 170 (1975)). Once BTV becomes established in a country, the virus is virtually impossible to eradicate (Erasmus, 51 Aust Vet J 209). The etiologic agent of bluetongue belongs to the family Reoviridae, genus *Orbivirus*.

The viral etiology of bluetongue was established by Theiler in 1906, (Erasmus, 51 Aust V e t J 165 (1975)). Since then several reports have appeared in the literature which (a) confirm the isolation of bluetongue virus from cattle, sheep, goats, and a number of wild ruminants and (b) the clinical and pathological features of the bluetongue diseases, and (c) describe infections resulting from different BTV serotypes. For example, see Onderstepoort (J Vet Sci Anim Indus 7 (1944); Komarov and Goldsmit, Refuah Vet 96 (1951); Price and Hardy, 124 J Am Med Assn 255 (1954); Shope et al, 111 J Exp Med 155 (1960); Livingston and Hardy, 25 AJVR 1958 (1964); Luedke et al 30 AJVR 511 (1969); Hourrigan et al, 51 Aust Vet J 170 (1975), Immunological control of bluetongue in the United States was first attempted by McKercher et al I18 AJVR 310 (1975), with a BTV International serotype 10 vaccine grown in fertile hen eggs. This product was patterned after that of Alexander, (J V et Sci Indus 231 (1947)), who first succeeded in propagating the bluetongue virus in chicken embryos.

Early vaccination protocols were routinely carried out in South Africa and Israel using an egg-attenuated polyvalent live virus vaccine containing a number of bluetongue strains. An egg-adapted vaccine produced by Cutter Laboratories and used in the United States has been taken off the market because of severe reactions in vaccinated sheep. Subsequently, Kemeny and Drehle, 22 AJVR 921 (1961), adapted the BTV International type 10 from eggs to bovine kidney cell cultures. This modified live virus vaccine, produced by Colorado Serum Company, is used for sheep in the United States.

There is a need for improvements in development of vaccines for use in immunizing ruminants, in particular, sheep and lambs against Bluetongue virus. The present invention addresses this need. The citation of any reference herein should not be deemed as an admission that such reference is available as prior art to the instant invention.

SUMMARY OF THE INVENTION

In accordance with the present invention, it has been found that bluetongue viruses can be twice inactivated using the methods described herein, and these twice inactivated viruses may be used in the preparation of vaccine and immunogenic compositions for immunizing ruminants against various strains and pathogenic serotypes of BTV. Moreover, it has been determined that particular combinations of adjuvants and excipients are effective for use in the compositions of the invention to elicit an effective immune response in the ruminants administered the compositions.

Accordingly, one aspect of the invention provides a composition for eliciting an immune response against Bluetongue virus (BTV) in an animal, the composition comprising an immunogenically effective amount of at least one strain of a twice inactivated Bluetongue virus and a biologically acceptable adjuvant.

In one embodiment, the twice inactivated BTV used in the compositions is inactivated a first time with an inactivating agent at a concentration of about 10 mM and inactivated a second time with an inactivating agent at a concentration of about 5 mM.

In one embodiment, the inactivating agent used to treat the BTV for use in the compositions is binary ethyleneimine (BEI).

In one embodiment, the composition comprises a strain of BTV that is serotype 4.

In one embodiment, the composition is a vaccine composition or an immunogenic composition.

In one embodiment, the animal to be treated with the composition is a ruminant selected from the group consisting of sheep, lambs, goats, cattle and deer.

In one embodiment, the animal to be treated with the composition is a sheep or lamb.

In one embodiment, the biologically acceptable adjuvant to be used with the composition is selected from the group consisting of one or more of aluminum hydroxide, saponin, SL-CD, Carbopol and SP-Oil.

In one embodiment, the biologically acceptable adjuvant to be used with the composition comprises a mixture of aluminum hydroxide and saponin. In one embodiment, the aluminum hydroxide is present at a concentration of between about 1% and about 10%. In one embodiment, the aluminum hydroxide is present at a concentration of between about 2% and about 5%. In one embodiment, the aluminum hydroxide is present at a concentration of about 3%.

In one embodiment, the immune response elicited with the compositions of the invention protects an animal against infection with, or reduces the severity of at least one symptom associated with an infection by a pathogenic strain of Bluetongue virus.

A second aspect of the invention provides a method for enhancing the immune response in an animal to Bluetongue virus, or for preventing or reducing at least one symptom associated with the disease, the method comprising the step of administering a single or multiple doses of the composition of the invention, as described above.

In one embodiment, the methods for enhancing the immune response in an animal to Bluetongue virus, or for preventing or reducing at least one symptom associated with the disease are useful in achieving such effect in a ruminant selected from the group consisting of sheep, lambs, goats, cattle and deer. In one embodiment, the ruminant is a sheep or lamb.

In one embodiment, the methods for enhancing the immune response in an animal to Bluetongue virus, or for preventing or reducing at least one symptom associated with the disease provide for the step of administering the compositions by parenteral administration. The parenteral administration step may be achieved by intramuscular injection.

In one embodiment, the methods for enhancing the immune response in an animal to Bluetongue virus, or for preventing or reducing at least one symptom associated with the disease provide for the step of administering the compositions by oral administration, which may be achieved by hand delivery or mass application.

A third aspect of the invention provides a method of preventing or ameliorating an outbreak of Bluetongue virus, which comprises the step of administering to an animal a composition of the invention.

In one embodiment, the method of preventing or ameliorating an outbreak of Bluetongue virus provides for treating an animal that is a ruminant selected from the group consisting of sheep, lambs, goats, cattle and deer. In one embodiment, the ruminant is a sheep or a lamb.

In one embodiment, the method of preventing or ameliorating an outbreak of Bluetongue virus provides for the step of administering the compositions of the invention by parenteral administration. The parenteral administration step may be achieved by intramuscular injection.

In one embodiment, the method of preventing or ameliorating an outbreak of Bluetongue virus provides for the step of administering the compositions of the invention by oral administration. The oral administration step may be achieved by hand delivery or mass application.

A fourth aspect of the invention provides a method of producing inactivated whole Bluetongue virus (BTV), the method comprising the steps of:
 a) treating the BTV with an inactivating agent using a 1:10 ratio of inactivating agent to BTV;
 b) homogenizing the inactivating agent/BTV mixture of step a) for at least 15 minutes;
 c) decanting the mixture of step b) into a sterile container and agitating the mixture for about 24 hours;
 d) treating the BTV a second time with an inactivating agent using a 1:20 ratio of inactivating agent to BTV;
 e) homogenizing the inactivating agent/BTV mixture of step d) for at least 15 minutes;
 f) decanting the mixture of step e) into a sterile container and agitating the mixture for about 48 hours; and
 g) neutralizing the inactivating agent to adjust the final pH to about 7.2;
wherein the method results in inactivation of the BTV while maintaining the immunogenicity of the BTV.

In one embodiment, the method for preparing twice-inactivated BTV, as described above, provides for the use of binary ethyleneimine (BEI) as an inactivating agent. In one embodiment, the final concentration of inactivating agent in step a), as noted above, is about 10 mM. In one embodiment, the final concentration of inactivating agent in step d), as noted above, is about 5 mM.

In one embodiment, the method described above for preparing twice inactivated whole BTV utilizes a Bluetongue virus that is serotype 4.

A fifth aspect of the invention provides for use of at least one twice inactivated strain of BTV for the preparation of a medicament for immunizing ruminants against various strains and serotypes of BTV. In one embodiment, the at least one twice inactivated strain of BTV for use in preparation of the medicament is serotype 4.

DETAILED DESCRIPTION OF THE INVENTION

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Accordingly, in the present application, there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel at al. (eds.), *Current Protocols in Molecular Biology*, John Wiley & Sons, Inc. (1994).

Although any methods and materials similar or equivalent to those described herein can be used in the practice or testing of the invention, the preferred methods and materials are now described. All publications mentioned herein are incorporated by reference in their entirety.

Definitions

The terms used herein have the meanings recognized and known to those of skill in the art, however, for convenience and completeness, particular terms and their meanings are set forth below.

The term "about" or "approximately" means within a statistically meaningful range of a value. Such a range can be within an order of magnitude, typically within 50%, more typically within 20%, more typically still within 10%, and even more typically within 5% of a given value or range. The allowable variation encompassed by the term "about" or "approximately" depends on the particular system under study, and can be readily appreciated by one of ordinary skill in the art.

"Adjuvant" means a composition comprised of one or more substances that enhances the immunogenicity of an antigen in a composition, typically a vaccine composition. An adjuvant can serve as a tissue depot that slowly releases the antigen and also as a lymphoid system activator that non-specifically enhances the immune response (Hood, et al., *Immunology, Second Ed.*, Menlo Park, Calif.: Benjamin/Cummings, 1984. p. 384). Often, a primary vaccination with an antigen alone, in the absence of an adjuvant, will fail to elicit a humoral or cellular immune response. Adjuvants include, but are not limited to, complete Freund's adjuvant, incomplete Freund's adjuvant, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alartyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, BCG (bacille Calmette-Guerin) and *Corynebacterium parvum*. Preferably, the adjuvant is biologically acceptable. In one embodiment of the invention, the composition is administered with a combination of two adjuvants, aluminum hydroxide and saponin.

Adjuvants employed in the compositions described herein are typically "biologically acceptable adjuvants" and, thus, may be used in combination with an inactivated BTV, such that the resulting compositions may be administered in vivo without concomitant toxicity to an animal. Exemplified herein are compositions including twice inactivated BTV in combination with one or more biologically acceptable adjuvants selected from the group consisting of aluminum hydroxide, saponin, SP-Oil, SL-CD, or Carbopol. In certain embodiments, two adjuvants are used to elicit the preferred immune response to BTV. In other embodiments, a mixture of a metabolizable oil such as one or more unsaturated terpene hydrocarbon(s) may be considered for use, for example squalene or squalane, and a polyoxyethylene-polypropylene block copolymer such as Pluronic®.

An inactivated strain of BTV or molecule derived therefrom is "antigenic" when it is capable of specifically interacting with an antigen recognition molecule of the immune system, such as an immunoglobulin (antibody) or T cell antigen receptor. Typically, an antigenic molecule is a polypeptide, or variant thereof, which contains an "epitope" of at least about five and typically at least about 10 amino acids. An antigenic portion of a polypeptide, also called herein the "epitope," can be that portion that is immunodominant for antibody or T cell receptor recognition, or it can be a portion used to generate an antibody to the molecule by conjugating the antigenic portion to a carrier polypeptide for immunization. A molecule that is antigenic need not be itself immunogenic, i.e., capable of eliciting an immune response without a carrier.

It is noted that in this disclosure, terms such as "comprises", "comprised", "comprising", "contains", "containing" and the like can have the meaning attributed to them in U.S. patent law; eg., they can mean "includes", "included", "including" and the like. Terms such as "consisting essentially of" and "consists essentially of" have the meaning attributed to them in U.S. patent law, eg., they allow for the inclusion of additional ingredients or steps that do not detract from the novel or basic characteristics of the invention, ie., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, eg., novel, nonobvious, inventive, over the prior art, eg., over documents cited herein or incorporated by reference herein. And, the terms "consists of" and "consisting of" have the meaning ascribed to them in U.S. patent law; namely, that these terms are closed ended.

An "immune response" to a vaccine or immunogenic composition is the development in a subject of a humoral and/or a cell-mediated immune response to molecules present in the antigen or vaccine composition of interest. For purposes of the present invention, a "humoral immune response" is an antibody-mediated immune response and involves the generation of antibodies with affinity for the antigen/vaccine of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatibility complex (MHC). This activates antigen-specific CD4+ T helper cells or CD8+ cytotoxic T lymphocyte cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al., J. Immunol. (1993) 151:4189-4199; Doe et al., Eur. J. Immunol. (1994) 24:2369-2376.

The "immunogenically effective amount" is the amount of whole inactivated BTV that will elicit an immune response in an animal. This amount will depend upon the species, breed, age, size, health status of the recipient animal and will be influenced by the previous exposure of the animal to one or more strain of BTV whether that one or more strain is a virulent strain or an avirulent strain. As used herein, an "immunogenically effective amount" of whole inactivated BTV, when employed in combination with one or more suitable adjuvants, is that amount of BTV that is sufficient to enhance the immunogenicity of the BTV and thus provides for protective immunity against challenge with a pathogenic or virulent BTV strain or serotype.

The term "immunogenic" refers to the ability of an antigen or a vaccine to elicit an immune response, either humoral or cell mediated, or both. As used herein, the term "immunogenic" means that the BTV is capable of eliciting a humoral and/or cellular immune response. An immunogenic strain is also antigenic. An immunogenic composition is a composition that elicits a humoral and/or cellular immune response when administered to an animal.

The term "immunogenic composition" relates to any pharmaceutical composition containing an antigen, eg. a microorganism, which composition can be used to elicit an immune response in a mammal. The immune response can include a T cell response, a B cell response, or both a T cell and B cell response. The composition may serve to sensitize the mammal by the presentation of antigen in association with MHC molecules at the cell surface. In addition, antigen-specific T-lymphocytes or antibodies can be generated to allow for the future protection of an immunized host. An "immunogenic composition" may contain a live, attenuated, or killed/inactivated vaccine comprising a whole microorganism or an immunogenic portion derived therefrom that induces either a cell-mediated (T cell) immune response or an antibody-mediated (B cell) immune response, or both, and may protect the animal from one or more symptoms associated with infection by the microorganism, or may protect the animal from death due to the infection with the microorganism.

The term "inactivated" refers to the non-infectious nature of the microorganisms to be used in a vaccine or immunogenic composition of the invention. In particular, those skilled in the art are aware of such materials that may be used to render a microorganism non-infectious for vaccine purposes, for example, BEI. In the present invention, particular methods have also been developed to render the Bluetongue virus non-infectious, but these methods have also been developed with particular emphasis on retaining the immunogenicity of the vaccine preparation, while at the same time resulting in complete inactivation of the virus preparation.

As used herein, the term "isolated" means that the referenced material is removed from its native environment. Thus, an isolated biological material can be free of some or all cellular components, i.e., components of the cells in which the native material occurs naturally (e.g., cytoplasmic or membrane component). A material is isolated if it is present in a cell extract or supernatant. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "parenteral administration" as used herein means administration by some other means than through the gastrointestinal tract, particularly to the introduction of substances into an organism by intravenous, subcutaneous, intramuscular, or intramedullary injection, but also to other non-oral and non-nasal routes of administration such as intraperitoneal injection or topical application.

The term "pathogenic" refers to the ability of any agent of infection, such as a bacterium or a virus, to cause disease. In the manner of the present invention, the term "pathogenic" refers to the ability of a Bluetongue virus (BTV), to cause a disease in ruminants, particularly sheep or lambs. A "non-pathogenic" microorganism refers to a microorganism that lacks the characteristics noted above for the "pathogenic" strains of BTV. The disease caused by BTV is often characterized by lesions in infected animals, which resemble infectious bovine virus diarrhea, vesicular stomatitis virus, malignant catarrhal fever, mycotic stomatitis, rinderpest, photosensitization, and foot and mouth disease. Bluetongue virus (BTV) has been incriminated as a cause of hydranencephaly in cattle and of infertility, abortion, and birth of defective young in cattle and sheep.

The term "pharmaceutically acceptable carrier" means a carrier approved by a regulatory agency of a Federal, a state government, or other regulatory agency, or listed in the U.S. Pharmacopeia or other generally recognized pharmacopeia for use in animals, including humans as well as non-human mammals. The term "carrier" refers to a diluent, adjuvant, excipient, or vehicle with which the pharmaceutical composition is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. The formulation should suit the mode of administration.

The term "protecting" refers to shielding eg. a mammal, in particular, a ruminant, for example, a sheep, a lamb, a goat or a cow, from infection or a disease, by inducing an immune response to a particular pathogen, eg. Bluetongue virus. Such protection is generally achieved following treating a mammal with the vaccine compositions described herein.

The term "purified" as used herein refers to material that has been isolated under conditions that reduce or eliminate the presence of unrelated materials, i.e., contaminants, including native materials from which the material is obtained. For example, a purified bacteria or protein is typically substantially free of host cell or culture components, including tissue culture or egg proteins, non-specific pathogens, and the like. As used herein, the term "substantially free" is used operationally, in the context of analytical testing of the material. Typically, purified material substantially free of contaminants is at least 50% pure; more typically at least 90% pure, and more typically still at least 99% pure. Purity can be evaluated by chromatography, gel electrophoresis, immunoassay, composition analysis, biological assay, and other methods known in the art. Methods for purification are well-known in the art. The term "substantially pure" indicates the highest degree of purity which can be achieved using conventional purification techniques known in the art.

"Saponins" are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Hemolysis of erythrocytes is an example of this phenomenon, which is a property of certain, but not all, saponins. Saponins are known as adjuvants in vaccines for systemic administration. The adjuvant and hemolytic activity of individual saponins has been extensively studied in the art (Lacaille-Dubois and Wagner, supra). For example, "Quil A" (derived from the bark of the South American tree *Quillaja Saponaria Molina*), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55, and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1). These structures have been reported to have adjuvant activity (EP 0 109 942 B1; WO 96/11711). The hemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-hemolytic fraction of Quil-A) which acts as a potent adjuvant for systemic vaccines. Use of QS21 is further described in Kensil et al. (1991, J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bamford et al., Vaccine, 10(9): 572-577, 1992). Saponins are also known to have been used in mucosally applied vaccine studies, which have met with variable success in the induction of immune responses. Quil-A saponin has previously been shown to have no effect on the induction of an immune response when antigen is administered intranasally (Gizurarson et al. 1994 Vaccine Research 3, 23-29), while other authors have used this adjuvant with success (Maharaj et al., Can. J. Microbial, 1986, 32(5):414-20. Chavali and Campbell, Immunobiology, 174(3):347-59). ISCOMs comprising Quil A saponin have been used in intragastric and intransal vaccine formulations and exhibited adjuvant activity (Mcl Mowat et al., 1991, Immunology, 72, 317-322; Mcl Mowat and Donachie, Immunology Today, 12, 383-385). QS21, the non-toxic fraction of Quil A, has also been described as an oral or intranasal adjuvant (Sumino et al., J. Virol., 1998, 72(6):4931-9, WO 98/56415). The use of other saponins in intranasal vaccination studies has been described. For example, *Chenopodium* quinoa saponins have been used in both intranasal and intragastric vaccines (Estrada et al., Comp. Immunol. Microbiol. Infect. Dis., 1998, 21(3):225-36).

The term "SL-CD" refers to a sulpholipo-cyclodextrin that falls within the family of cyclodextrin adjuvants described in U.S. Pat. Nos. 6,610,310 and 6,165,995. Typically, SL-CD is formulated in a mixture with a metabolizable oil such as one or more unsaturated terpene hydrocarbons, for example, squalane and preferably with a non-ionic surfactant, such as polyoxyethylene sorbitan monooleate.

The term "SP-Oil" refers to an adjuvant that is an oil emulsion comprising: 1% to 3% vol/vol of polyoxyethylene-polyoxypropylene block copolymer; 2% to 6% vol/vol of squalane; 0.1% to 0.5% vol/vol of polyoxyethylene sorbitan monooleate; and a buffered salt solution.

The term "ruminant" refers to any variety of hoofed, even footed, and usually horned mammals that characteristically have their stomachs divided into four sections, including cows, sheep, giraffes, goats and deer.

As used herein, "treatment" (including variations thereof, for example, "treat" or "treated") refers to any one or more of the following: (i) the prevention of infection or reinfection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided which treat, including prophylactically and/or therapeutically immunize, a host animal against a viral infection. The methods of the present invention are useful for conferring prophylactic and/or therapeutic immunity to a mammal, preferably a ruminant, such as a sheep, lamb, cow or goat. The methods of the present invention can also be practiced on mammals for biomedical research applications.

The term "twice inactivated" refers to the use of particular methods as described in the present invention, for rendering the BTV non-infectious, while retaining the immunogenicity of the virus preparation. More particularly, the BTV of the present invention is twice inactivated by using two rounds of incubation of BTV with BEI, wherein the first step of inactivation is accomplished by incubating the BTV with BEI at a concentration of 10 mM for 24 hours, and whereby the second round of inactivation is accomplished by incubating the BTV with BEI at a concentration of 5 mM for 48 hours.

The terms "vaccine" or "vaccine composition", which are used interchangeably, refer to pharmaceutical compositions comprising at least one immunogenic composition that induces an immune response in an animal. A vaccine or vaccine composition may protect the animal from disease or possible death due to an infection, and may or may not include one or more additional components that enhance the immunological activity of the active component. A vaccine or vaccine composition may additionally comprise further components typical to pharmaceutical compositions. A vaccine or vaccine composition may additionally comprise further components typical to vaccines or vaccine compositions, including, for example, an adjuvant or an immunomodulator. The immunogenically active component of a vaccine may comprise complete live organisms in either their original form, or as attenuated organisms in a modified live vaccine, or organisms inactivated by appropriate methods in a killed or inactivated vaccine, or subunit vaccines comprising one or more immunogenic components of the virus, or genetically engineered, mutated or cloned vaccines prepared by methods known to those skilled in the art. A vaccine or vaccine composition may comprise one or simultaneously more than one of the elements described above.

General Description

Due to its potential impact on the large animal industry, the development of a vaccine against Bluetongue virus is of major importance, particularly to the cattle and sheep industry. Pathogenic strains, even if attenuated, are likely to be of limited value due to the usual tendency of a live virus to revert to its virulent state. Moreover, it is imperative that if an inactivated vaccine is to be of commercial use, the virus must be fully inactivated to ensure an adequate safety profile for the animal. Furthermore, it is also important that the inactivation does not have a detrimental effect on the immunogenicity of the virus or components of the virus responsible for inducing an immune response.

Accordingly, the present invention relates to compositions and methods for immunizing an animal, in particular a ruminant, such as a sheep, or lamb, or cow against a Bluetongue virus (BTV) infection, or for reducing the severity of at least one symptom of the disease. The composition comprises at least one twice inactivated strain of BTV and a biologically acceptable adjuvant. In certain embodiments, a combination of at least two biologically acceptable adjuvants is utilized.

In one embodiment of the present invention, the methods provide for immunizing a ruminant against a pathogenic BTV and for protecting the animal against such infection.

In particular, the methods of the present invention provide for the use of a vaccine or immunogenic composition comprising at least one whole and twice inactivated strain of BTV for immunizing a rurriinant against infection with BTV. In one embodiment, the methods of the present invention provide for the use of a vaccine or immunogenic composition comprising serotype 4 of BTV for immunizing a ruminant against infection with BTV.

The Bluetongue virus to be used in the compositions and methods of the invention may be obtained from any known depository, which retains stocks of the various serotypes of BTV, such as the American Type Culture Collection (ATCC). For example, the ATCC maintains several different strains of BTV, which are listed in their catalogue with the following designated accession numbers: VR-187 (serotype 10), VR-872 (serotype 11), VR-873 (serotype 13), VR-875 (serotype 17), VR-983 (serotype 2), VR-1231 (serotype 10), VR-1231AF (serotype 10) and VR-1231CAF (murine serotype 10). Furthermore, serotype 4 has been described by Mertens et al. (Mertens, P P, et al. (Virology, 161(2): 438-447, (1987)) and Breard et al. (Breard, E. et al. Virus Res., 125(2): 191-197, (2007)).

Methods of Inactivation

Inactivated virus vaccines or immunogenic compositions may be prepared by treating the BTV with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection. In one particular embodiment, binary ethyleneimine (BEI) is the means used for inactivation.

In certain aspects of the invention, methods for producing the twice inactivated form of at least one whole BTV are provided. The method comprises the steps of:
a) treating the BTV with an inactivating agent using a 1:10 ratio of inactivating agent to BTV;
b) homogenizing the inactivating agent/BTV mixture of step a) for at least 15 minutes;
c) decanting the mixture of step b) into a sterile container and agitating the mixture for about 24 hours;
d) treating the BTV a second time with an inactivating agent using a 1:20 ratio of inactivating agent to BTV;
e) homogenizing the inactivating agent/BTV mixture of step d) for at least 15 minutes;
f) decanting the mixture of step e) into a sterile container and agitating the mixture for about 48 hours; and
g) neutralizing the inactivating agent to adjust the final pH to about 7.2;

wherein the method results in inactivation of the BTV while maintaining the immunogenicity of the BTV.

In one embodiment, the method for preparing twice inactivated BTV, as described above, provides for the use of binary ethyleneimine (BEI) as an inactivating agent. In one embodiment, the final concentration of inactivating agent in step a), as noted above, is about 10 mM. In one embodiment, the final concentration of inactivating agent in step d), as noted above, is about 5 mM.

In one embodiment, the method described above for preparing twice inactivated whole BTV utilizes a Bluetongue virus that is serotype 4.

Vaccine or Immunogenic Compositions and Methods of Use

An immunogenically effective amount of the vaccines of the present invention is administered to a ruminant in need of protection against infection with Bluetongue virus (BTV). The immunogenically effective amount or the immunogenic amount that inoculates the ruminant can be easily determined or readily titrated by routine testing. An effective amount is one in which a sufficient immunological response to the vaccine is attained to protect the animal exposed to the virus. Preferably, the animal is protected to an extent in which one to all of the adverse physiological symptoms or effects of the viral disease are significantly reduced, ameliorated or totally prevented.

The vaccine or immunogenic composition can be administered in a single dose or in repeated doses. Methods are known in the art for determining or titrating suitable dosages of active antigenic agent based on the weight of the animal, concentration of the antigen and other typical factors.

Desirably, the vaccine or immunogenic composition is administered to a ruminant not yet exposed to the virus. The vaccine containing the whole and twice inactivated virus or other antigenic forms thereof can conveniently be administered intranasally, transdermally (i.e., applied on or at the skin surface for systemic absorption), parenterally, etc. The parenteral route of administration includes, but is not limited to, intramuscular, intravenous, intraperitoneal, intradermal (i.e., injected or otherwise placed under the skin) routes and the like. Since the intramuscular and intradermal routes of inoculation have been successful in other studies using viral infectious DNA clones (E. E. Sparger et al., "Infection of cats by injection with DNA of feline immunodeficiency virus molecular clone," Virology 238:157-160 (1997); L. Willems et al., "In vivo transfection of bovine leukemia provirus into sheep," Virology 189:775-777 (1992)), these routes are most preferred, in addition to the practical intranasal route of administration.

When administered as a liquid, the present vaccine may be prepared in the form of an aqueous solution, syrup, an elixir, a tincture and the like. Such formulations are known in the art and are typically prepared by dissolution of the antigen and other typical additives in the appropriate carrier or solvent systems. Suitable "physiologically acceptable" carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions that contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of porcine body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives that can be employed in the present vaccine include, but are not limited to, dextrose, conventional antioxidants and conventional chelating agents such as ethylenediamine tetraacetic acid (EDTA). Parenteral dosage forms must also be sterilized prior to use.

Adjuvants

The twice inactivated Bluetongue virus may be delivered with an adjuvant. In one embodiment, the vaccine is a whole and twice killed/inactivated BTV, which is administered with an adjuvant. An adjuvant is a substance that increases the immunological response of the animal to the vaccine. The adjuvant may be administered at the same time and at the same site as the vaccine, or at a different time, for example, as a booster. Adjuvants also may advantageously be administered to the ruminant in a manner or at a site different from the manner or site in which the vaccine is administered. Suitable adjuvants include, but are not limited to, aluminum hydroxide (alum), Alhydrogel® (Brenntag Biosector, Frederikssund, Denmark), immunostimulating complexes (ISCOMS), non-ionic block polymers or copolymers, cytokines (like IL-1, IL-2, IL-7, IFN-α, IFN-62, IFN-γ, etc.), saponins (including Quillaia A, or Quil A ((Brenntag Biosector, Frederikssund, Denmark), monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde. In one embodiment, the vaccine composition is delivered with a combination of at least two adjuvants. In one embodiment, the vaccine composition is delivered with a combination of both aluminum hydroxide (Alhydrogel®) and saponin (Quil A).

Assays for Measuring Immune Responses

The functional outcome of vaccinating a ruminant against BTV can be assessed by suitable assays that monitor induction of cellular or humoral immunity or T cell activity. These assays are known to one skilled in the art, but may include measurement of cytolytic T cell activity using for example, a chromium release assay. Alternatively, T cell proliferative assays may be used as an indication of immune reactivity or lack thereof. In addition, in vivo studies can be done to assess the level of protection in a mammal vaccinated against a pathogen using the methods of the present invention. Typical in vivo assays may involve vaccinating an animal with an antigen, such as the virus described herein. After waiting for a time sufficient for induction of an antibody or T cell response to occur, generally from about one to two weeks after injection, the animals will be challenged with the antigen, such as either a virus, and amelioration of one or more symptoms associated with the viral infection, or survival of the animals is monitored. A successful vaccination regimen against BTV will result in significant decrease in one or more symptoms associated with the viral infection, or a decrease in viremia, or a decrease in the number or severity of lesions associated with a viral infection, or survival when compared to the non-vaccinated controls. Serum may also be collected to monitor levels of antibodies generated in response to the vaccine injections, as measured by methods known to those skilled in the art.

EXAMPLES

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. All parts and percents referred to herein are on a weight basis and all temperatures are expressed in degrees centigrade unless otherwise specified.

Example 1

The Manufacturing Process

General Description

The manufacturing process is carried out in conditions of sterility, following the instructions of the Standard Manufacturing Method described below. Before the start of the operations defined as aseptic in the Standard Manufacturing Method, the correct operation condition of the air filtration installations and laminar flow cabinets is verified, and it is confirmed that the materials used in the process have been duly sterilized in autoclave or by filtration, or disinfected according to the established methods. Aseptic operations are conducted following established sterile manipulation techniques.

Description of Each Step of the Manufacturing Process

Manufacturing Method of the Final Antigen (Passage 3)

Obtainment of BHK-21 Cell Cultures

The BHK-21 cells (working cell stock or WCS) are stored frozen in liquid nitrogen. The WCS cryotubes are thawed by means of rapid thawing to +37° C. and then it is inoculated in a culture flask containing culture medium (MEM-Glasgow+ irradiated bovine calf serum).

The culture flask is incubated at +37±1° C. After at least 5 hours from the moment of inoculation, the medium is removed from the flask and new culture medium of the same composition is added, previously brought to a temperature of +37±1° C.

The culture is observed periodically, and its evolution (confluence) and cell morphology are recorded From this culture flask, in order to obtain the necessary flasks for production, the required subcultures are carried out at intervals of 3-5 days.

Subcultures are carried out by means of trypsinization of the culture with a solution of freshly prepared trypsin; a cell suspension count is done by vital staining (Trypan Blue) in Neubauer chamber. The cell suspension is then diluted in sterile culture medium contained in tanks or flasks, by means of magnetic agitation, and it is distributed in culture flasks.

The culture medium is adjusted to pH 7.2±0.2 at the start of the culture operation in roller flasks.

Once the last culture has been trypsinzed and centrifuged, the cell suspension is delivered to the section where antigens are manufactured.

Manufacture of Final Antigen (Passage 3)
Production of Passage 2 Antigen (Inoculum)

For the production of a batch of final antigen (passage 3), the inoculum (passage 2 antigen) is prepared according to the following method:

The working seed virus (WSV) is stored frozen at −70±10° C. From the WSV, 2 passages are done in order to obtain the inoculum. On the first passage a potency control is conducted, and on the second one sterility and potency controls are done after the freezing operation.

Passage 1 Antigen (Pre-Inoculum)

In one flask with BHK-21 cells at 2-3 days of culture, the culture medium is removed and substituted with infection medium (suspension of WSV in MEM-Glasgow).

The culture is incubated at +37±1° C.

When the cytopathic effect (CPE) is over 60%, the flask is placed in agitation in order to facilitate cell monolayer detachment, and then frozen at −70±10° C.

Passage 2 Antigen (Inoculum)

Passage 1 antigen is diluted in MEM-Glasgow. The culture medium of necessary growth flasks with BHK-21 cells at 2-3 days' culture is removed and substituted with the prepared virus suspension, and then placed in an incubator at +37±1° C.

When the CPE is over 60%, the flasks are placed in agitation in order to facilitate cell monolayer detachment, and then frozen at −70±10° C.

Culture Inoculation, Infection and Collection of Final Antigen (Passage 3)

MEM-Glasgow, BHK-21 cell suspension from the culture flasks and irradiated bovine calf serum are mixed and homogenized in a sterile container, under agitation.

Once the suspension is homogenized, a cell count is done in a Neubauer chamber.

With this suspension, the necessary flasks are inoculated and incubated at +37±1° C.

At 2-3 days of culture, the culture medium is removed from each flask and substituted with the infection medium: MEM-Glasgow+passage 2 antigen (inoculum). The infected flasks are then incubated under rotation movement at +37±1° C.

When CPE is over 60%, the flasks are placed in agitation in order to facilitate cell monolayer detachment, cultures are collected and homogenized, and the pH is verified. If necessary, adjusting with hydrochloric acid is done to obtain a pH of 7.2±0.2, and the collected final antigen (passage 3) is then inactivated.

Culture Process Characteristics

Culture is done in roller flasks.

Cell counts are done in a Neubauer chamber, after the sample has been diluted 1/2 with Trypan Blue.

Cultures are incubated at +37±1° C., turning over 12-14 times per hour.

The state and evolution of the culture is observed periodically, and cell morphology is observed with an inverted microscope.

Throughout the manufacturing process of the final antigen (passage 3), environmental controls are carried out in the work rooms by means of taking air samples during rest periods and manufacturing periods, and also exposition and contact plaques are analyzed in order to control the working equipment.

Sampling

Passage 1 antigen: Samples are taken of passage 1 antigen for a potency control by the Quality Control Department.

Passage 2 antigen: Samples are taken of passage 2 antigen for potency and sterility controls by the Quality Control Department.

Passage 3 antigen: Samples are taken of passage 3 antigen for potency, sterility and identity controls by the Quality Control Department.

Manufacture of the Inactivated Antigen

The process of inactivation of the final antigen lasts for a total of 72 hours, and the concentration of BEI used is 15 mM.

Final antigen is inactivated by adding BEI 0.1M at a proportion of 100 ml per liter of antigen being inactivated (final concentration 10 mM).

After the addition of the BEI, the mixture is homogenized for at least 15 minutes and the pH is verified. After the homogenization process, the mixture is decanted into a sterile container where it is kept in agitation, at 37±1° C., for 24 hours.

After 24 hours, a second inactivation of the final antigen is carried out by means of adding BEI 0.1M at a proportion of 50 ml per liter of antigen being inactivated (final concentration 5 mM). After the second addition of BEI, the process is repeated under the same conditions as described above for the first addition, but maintaining the mixture in agitation for 48 hours.

Neutralization of Residual BEI
Neutralization

Once the inactivation process has been completed, 1M sodium thiosulphate solution is added at the proportion of 5 ml per liter of inactivated antigen (final concentration 5 mM), in order to neutralize the BEI.

After the mixture has been homogenized, the pH is verified. If necessary, an adjustment is done with hydrochloric acid, to obtain a pH of 7.2±0.2.

Calculation of the Theoretical Titer of the Inactivated and Neutralized Antigen

To calculate the theoretical titer of the inactivated and neutralized antigen, the titer of the antigen previous to inactivation and the dilution factor that represent the additions of BEI in the inactivation process and of sodium thiosulphate in the neutralization process are taken into account.

For each liter of antigen, 100 ml of a solution of BEI 0.1 M are added to the first inactivation, and an additional 55 ml to the second inactivation. This way, 1000 ml of final antigen become 1155 ml of inactivated antigen. Immediately, in the process of neutralization, 5 ml of a solution of 1M sodium thiosulphate is added per liter of inactivated antigen. This way, the 1155 ml of inactivated antigen become 1161 ml of inactivated and neutralized antigen.

The inactivation and neutralization processes represent a total dilution of final antigen of 1/1.16 (1000 ml of final antigen become 1161 ml of inactivated and neutralized antigen). For this reason, it is considered that antigen with a standard titer previous to inactivation of $10^{7.2}$ TCID$_{50}$/ml, has a theoretical titer after inactivation and neutralization of $10^{7.2}$/1.16.

Sampling

Samples are taken of the inactivated and neutralized antigen for the Quality Control Department, for sterility and inactivation controls.

Example 2

Adjuvant Selection According to the Effect on Viremia Reduction after Challenge Pre-Immunogenicity Experiment in 2-Month Old Lambs Animals were vaccinated by the subcutaneous route (2 mL) and revaccinated 3 weeks later.

Animals vaccinated with vaccines A-3, B-3 and C-3 were challenged 7-8 weeks after re-vaccination (challenge dose=$10^7$ TCID$_{50}$ of live virus/animal). None of the challenged animals were protected. However, a viremia reduction was observed only in animals vaccinated with Alhydrogel (aluminium hydroxide) and Quil-A (saponin) as adjuvant.

TABLE 1

BTV PRE-IMMUNO VACCINES COMPOSITION

| *Inactivated BTV (TCID$_{50}$/ml) | Adjuvant | Batch |
|---|---|---|
| $10^6$ | | A-1 |
| $10^{6.7}$ ($5 \times 10^6$) | Alhydrogel/Quil-A (2 mg Al$^{2+}$/dose) | A-2 |
| $10^7$ | | A-3 |
| $10^6$ | | B-1 |
| $10^{6.7}$ ($5 \times 10^6$) | SL-CD adjuvant 20% | B-2 |
| $10^7$ | | B-3 |
| $10^6$ | | C-1 |
| $10^{6.7}$ ($5 \times 10^6$) | SP oil 5% | C-2 |
| $10^7$ | | C-3 |

*Cell culture supernatant. Total inactivation process 144 h [(10 mM BEI × 72 h) × 2]

Antibody Response after Vaccination

TABLE 2

PERCENTAGE OF POSITIVE ANIMALS (ELISA TEST)

| | GROUP | | | | | | | | | |
|---|---|---|---|---|---|---|---|---|---|---|
| | A1 | A2 | A3 | B1 | B2 | B3 | C1 | C2 | C3 | Control |
| No. ANIMALS | 11 | 11 | 11 | 10 | 11 | 11 | 11 | 9 | 11 | 11 |
| D + 3 WPV | 0% | 27% | 0% | 10% | 9% | 0% | 0% | 0% | 0% | 0% |
| D + 1 WPRV | 82% | 73% | 100% | 40% | 64% | 82% | 9% | 44% | 64% | 0% |
| D + 2 WPRV | 55% | 64% | 82% | 30% | 36% | 27% | 9% | 22% | 55% | 0% |
| D + 3 WPRV | 64% | 82% | 100% | 10% | 45% | 36% | 9% | 33% | 64% | 0% |
| D + 4 WPRV | 27% | 45% | 73% | 40% | 27% | 27% | 9% | 13% | 30% | 0% |

*Blocking ELISA using a VP7 specific MAb
WPV = Weeks post-vaccination WPRV = Weeks post-revaccination Challenge Results Animals vaccinated with batches A-3, B-3 and C-3 were challenged (5 animals of each group) at 7-8 weeks after re-vaccination. Two non-vaccinated controls were also challenged.

Bluetongue virus (BTV) was detected in blood samples by a real-time reverse transcription-polymerase chain reaction (RT-PCR) assay performed in the Laboratorio Central de Veterinaria (Algete, Spain). (Miguel Angel Jiménez-Clavero et al. (2006). J Vet Diagn Invest 18:7-17). Blood samples were taken at 4 and 7 days after infection (D+4 p.i. and D+7 p.i.). Blood samples treatment, total nucleic acid extraction following a 96-well nucleic acid extraction method and real-time RT-PCR, were performed as described by Miguel Angel Jiménez-Clavero et al., 2006 (J. Vet. Diagn. Invest. 18:7-17).

For the PCR analysis the threshold cycle was provided (Ct). Samples were considered positive for BTV if they yielded Ct values lower than 36. Samples that yielded Ct values between 36 and 40 were considered uncertain.

| | | | |
|---|---|---|---|
| Ct = Threshold cycle | | Ct results interpretation: | |
| SD = Standard deviation | TC < 36 | Positive | (Detection of virus) |
| CV % = Coefficient of variation | 36 < TC < 40 | Uncertain | |
| Group A3 | $10^7$ TCID$_{50}$ of BTiV/Dose - Adjuvant: Alhydrogel/Quil-A | | |
| Group B3 | $10^7$ TCID$_{50}$ of BTiV/Dose - Adjuvant: SL-CD | | |
| Group C3 | $10^7$ TCID$_{50}$ of BTiV/Dose - Adjuvant: SP oil | | |
| Group Cont | Control group (non-vaccinated) | | |

TABLE 3

Real-time fluorogenic RT-PCR results at 4 days post-challenge (D + 4 p.i.)

| | | (Blood samples) | |
|---|---|---|---|
| Group | Ref. FDV | Ct | Interpretation |
| A3 | 179 | 37.12 | Uncertain |
| A3 | 190 | 32.24 | Positive |
| A3 | 198 | 30.33 | Positive |
| A3 | 211 | 30.30 | Positive |
| A3 | 219 | 29.87 | Positive |
| TC Mean | | 31.97 | |

TABLE 3-continued

Real-time fluorogenic RT-PCR results at 4 days post-challenge (D + 4 p.i.)

| | | (Blood samples) | |
|---|---|---|---|
| Group | Ref. FDV | Ct | Interpretation |
| SD | | 3.02 | |
| CV % | | 9.45 | |
| B3 | 183 | 28.24 | Positive |
| B3 | 206 | 27.94 | Positive |
| B3 | 223 | 29.07 | Positive |
| B3 | 243 | 27.47 | Positive |
| TC Mean | | 28.18 | |
| SD | | 0.67 | |
| CV % | | 2.39 | |

TABLE 3-continued

Real-time fluorogenic RT-PCR results
at 4 days post-challenge (D + 4 p.i.)

| Group | Ref. FDV | (Blood samples) Ct | Interpretation |
|---|---|---|---|
| C3 | 162 | 30.15 | Positive |
| C3 | 174 | 26.15 | Positive |
| C3 | 175 | 30.67 | Positive |
| C3 | 241 | 30.07 | Positive |
| C3 | 254 | 29.27 | Positive |
| TC Mean | | 29.26 | |
| SD | | 1.81 | |
| CV % | | 6.19 | |
| Cont. | 225 | 31.67 | Positive |
| TC Mean | | 31.67 | |
| SD | | — | |
| CV % | | — | |

Ref. FDV = Reference number of the animal

TABLE 4

Real-time fluorogenic RT-PCR results
at 7 days post-challenge (D + 7 p.i.)

| Group | Ref. FDV | (Blood samples) Ct | Interpretation |
|---|---|---|---|
| A3 | 179 | 32.99 | Positive |
| A3 | 190 | 29.21 | Positive |
| A3 | 198 | — | Negative |
| A3 | 211 | 31.7 | Positive |
| A3 | 219 | 28.66 | Positive |
| TC Mean | | 30.64 | |
| SD | | 2.05 | |
| CV % | | 6.69 | |
| B3 | 183 | 26.62 | Positive |
| B3 | 206 | 31.17 | Positive |
| B3 | 223 | 26.88 | Positive |
| B3 | 243 | 26.94 | Positive |
| TC Mean | | 27.90 | |
| SD | | 2.18 | |
| CV % | | 7.82 | |
| C3 | 162 | 29.61 | Positive |
| C3 | 174 | 27.12 | Positive |
| C3 | 175 | — | Negative |
| C3 | 241 | 29.86 | Positive |
| C3 | 254 | 28.26 | Positive |
| TC Mean | | 28.71 | |
| SD | | 1.27 | |
| CV % | | 4.43 | |
| Cont. | | — | |
| Cont. | 225 | 29.02 | Positive |
| TC Mean | | 29.02 | |
| SD | | — | |
| CV % | | — | |

Ref. FDV = Reference number of the animal

For comparison between vaccinated and non-vaccinated animals taking into account real-time RT-PCR results, the mean Ct from the control group were subtracted from the mean Ct from each of the different vaccinated groups. (Miguel Angel Jiménez-Clavero et el. (2006)). J Vet Diagn Invest 18:7-17) demonstrated that the detection achieved by the real-time RT-PCR assay showed a linear relationship between signal and the quantity of viral RNA present in the sample (equivalent $TCID_{50}$ infectious units per milliliter) on a log scale (correlation coefficient of 0.9948, and a slope of −3.334). For that reason, the Ct mean difference between each vaccinated group and the control group was divided by 3.334 and the log of the resultant number was calculated.

TABLE 5

Comparison between vaccinated and non-vaccinated animals according
to the real-time RT-PCR results at 4 days post-challenge (D + 4 p.i.)

| Group | Ct Mean/Group | SD | CV |
|---|---|---|---|
| A3 | 31.97 | 3.02 | 9.45 |
| B3 | 28.18 | 0.67 | 2.39 |
| C3 | 29.26 | 1.81 | 6.19 |
| Control | 31.67 | — | — |

| Ct differences | Ct differences | Ct dif/3.334 | log (Ct dif/3.334) |
|---|---|---|---|
| A3-Control | 0.30 | 0.09 | 1.23 |
| B3-Control | −3.49 | −1.05 | 0.09 |
| C3-Control | −2.41 | −0.72 | 0.19 |

Comparison between vaccinated and non-vaccinated animals according
to the real-time RT-PCR results at 7 days post-challenge (D + 7 p.i.)

| Group | Ct Mean/Group | SD | CV |
|---|---|---|---|
| A3 | 30.64 | 2.05 | 6.69 |
| B3 | 27.90 | 2.18 | 7.82 |
| C3 | 28.71 | 1.27 | 4.43 |
| Control | 29.02 | | |

| Ct differences | Ct differences | Ct dif/3.334 | log (Ct dif/3.334) |
|---|---|---|---|
| A3-Control | 1.62 | 0.49 | 3.06 |
| B3-Control | −1.12 | −0.34 | 0.46 |
| C3-Control | −0.31 | −0.09 | 0.81 |

Conclusions

The calculated numbers [log(Ct dif/3,334)] express the relationship between control and vaccinated groups. At 7 days post-challenge:
1. Animals vaccinated with the adjuvant Alhydrogel and Quil-A had 3-fold less virus in blood than the control group (there are data of only 1 non-vaccinated animal)
2. Animals vaccinated with SP-oil or SL-CD adjuvant did not show any viremia reduction in comparison with the control group (there are data of only 1 non-vaccinated animal)
3. Alhydrogel (aluminium hydroxide) and Quil-A (saponin) is a better adjuvant than SP-oil or SLCD

Example 3

Antigen Concentration Effect on Viremia Reduction

Pre-Immunogenicity Experiment in 2-Month Old Lambs

Animals were vaccinated by the subcutaneous route (2 mL) and revaccinated 3 weeks later.

Animals vaccinated with vaccines A-1, A-2 and A-3 were challenged 5-6 weeks after re-vaccination (challenge dose=$10^7$ $TCID_{50}$ of live virus/animal). None of the challenged animals were protected. However, a viremia antigen dose dependent reduction was observed.

TABLE 6

| BTV PRE-IMMUNO VACCINES COMPOSITION | | |
|---|---|---|
| *Inactivated BTV ($TCID_{50}$/ml) | Adjuvant | Batch |
| $10^6$ | Alhydrogel/Quil-A (2 mg $Al^{2+}$/dose) | A-1 |
| $10^{6.7}$ ($5 \times 10^6$) | | A-2 |
| $10^7$ | | A-3 |
| $10^6$ | SL-CD adjuvant 20% | B-1 |
| $10^{6.7}$ ($5 \times 10^6$) | | B-2 |
| $10^7$ | | B-3 |

TABLE 6-continued

BTV PRE-IMMUNO VACCINES COMPOSITION

| *Inactivated BTV (TCID$_{50}$/ml) | Adjuvant | Batch |
|---|---|---|
| $10^6$ | SP oil 5% | C-1 |
| $10^{6.7}$ ($5 \times 10^6$) | | C-2 |
| $10^7$ | | C-3 |

*Cell culture supernatant. Total inactivation process 144 h [(10 mM BEI × 72 h) × 2]

Antibody Response after Vaccination

TABLE 7

PERCENTAGE OF POSITIVE ANIMALS (ELISA TEST)

| | GROUP | | | | | | | | | |
|---|---|---|---|---|---|---|---|---|---|---|
| | A1 | A2 | A3 | B1 | B2 | B3 | C1 | C2 | C3 | Control |
| No. ANIMALS | 11 | 11 | 11 | 10 | 11 | 11 | 11 | 9 | 11 | 11 |
| D + 3 WPV | 0% | 27% | 0% | 10% | 9% | 0% | 0% | 0% | 0% | 0% |
| D + 1 WPRV | 82% | 73% | 100% | 40% | 64% | 82% | 9% | 44% | 64% | 0% |
| D + 2 WPRV | 55% | 64% | 82% | 30% | 36% | 27% | 9% | 22% | 55% | 0% |
| D + 3 WPRV | 64% | 82% | 100% | 10% | 45% | 36% | 9% | 33% | 64% | 0% |
| D + 4 WPRV | 27% | 45% | 73% | 40% | 27% | 27% | 9% | 13% | 30% | 0% |

*Blocking ELISA using a VP7 specific MAb
WPV = Weeks post-vaccination  WPRV = Weeks post-revaccination

Challenge Results

Animals vaccinated with batches A-1, A-2 and A-3 were challenged (5 animals of each group) at 5-6 weeks after re-vaccination. Two non-vaccinated controls were also challenged.

Bluetongue virus (BTV) was detected in blood samples by a real-time reverse transcription-polymerase chain reaction (RT-PCR) assay performed in the Laboratorio Central de Veterinaria (Algete, Spain). (Miguel Angel Jiménez-Clavero et al. (2006). J Vet Diagn Invest 18:7-17). Blood samples were taken at 3 and 5 days after infection (D+3 p.i. and D+5 p.i.). Blood samples treatment, total nucleic acid extraction following a 96-well nucleic acid extraction method and real-time RT-PCR, were performed as described by Miguel Angel Jiménez-Clavero et al., 2006 (J. Vet. Diagn. Invest. 18:7-17). For the PCR analysis the threshold cycle was provided (Ct). Samples were were considered positive for BTV if they yielded Ct values lower than 36. Samples that yielded Ct values between 36 and 40 were considered uncertain.

| Ct = Threshold cycle | Ct results interpretation: | | |
|---|---|---|---|
| SD = Standard deviation | TC < 36 | Positive | (DETECTION OF VIRUS) |
| CV % = Coefficient of variation | 36 < TC < 40 | Uncertain | |

| Group A1 | $10^6$ TCID$_{50}$ of BTiV/Dose - Adjuvant: Alhydrogel/Quil-A |
|---|---|
| Group A2 | $10^{6.7}$ TCID$_{50}$ of BTiV/Dose - Adjuvant: Alhydrogel/Quil-A |
| Group A3 | $10^7$ TCID$_{50}$ of BTiV/Dose - Adjuvant: Alhydrogel/Quil-A |
| Group Cont | Control group (non-vaccinated) |

TABLE 8

Real-time fluorogenic RT-PCR results at 3 days post-challenge (D + 3 p.i.)

(Blood samples)

| Group | Ref. FDV | Ct | Interpretation |
|---|---|---|---|
| A1 | 155 | 36.68 | Uncertain |
| A1 | 167 | 35.11 | Positive |
| A1 | 202 | 37.68 | Uncertain |

TABLE 8-continued

Real-time fluorogenic RT-PCR results at 3 days post-challenge (D + 3 p.i.)

(Blood samples)

| Group | Ref. FDV | Ct | Interpretation |
|---|---|---|---|
| A1 | 232 | 33.46 | Positive |
| A1 | 246 | 36.20 | Uncertain |
| TC Mean | | 35.83 | |
| SD | | 1.61 | |
| CV % | | 4.50 | |
| A2 | 224 | — | Negative |
| A2 | 233 | 37.96 | Uncertain |
| A2 | 255 | 35.04 | Positive |
| A2 | 257 | — | Negative |
| A2 | 259 | 38.76 | Uncertain |
| TC Mean | | 37.25 | |
| SD | | 1.96 | |
| CV % | | 5.26 | |

TABLE 8-continued

Real-time fluorogenic RT-PCR results
at 3 days post-challenge (D + 3 p.i.)

(Blood samples)

| Group | Ref. FDV | Ct | Interpretation |
|---|---|---|---|
| A3 | 210 | 35.79 | Positive |
| A3 | 220 | 37.56 | Uncertain |
| A3 | 245 | 36.03 | Uncertain |
| A3 | 251 | 37.65 | Uncertain |
| A3 | 260 | 34.45 | Positive |
| TC Mean | | 36.30 | |
| SD | | 1.34 | |
| CV % | | 3.69 | |
| Cont | 203 | 33.10 | Positive |
| Cont | 208 | 38.85 | Uncertain |
| TC Mean | | 35.98 | |
| SD | | 18.86 | |
| CV % | | 52.43 | |

Ref. FDV = Reference number of the animal

TABLE 9

Real-time fluorogenic RT-PCR results
at 5 days post-challenge (D + 5 p.i.)

(Blood samples)

| Group | Ref. FDV | Ct | Interpretation |
|---|---|---|---|
| A1 | 155 | 28.54 | Positive |
| A1 | 167 | 31.85 | Positive |
| A1 | 202 | 27.72 | Positive |
| A1 | 232 | 29.04 | Positive |
| A1 | 246 | 26.12 | Positive |
| TC Mean | | 28.65 | |
| SD | | 2.10 | |
| CV % | | 7.34 | |
| A2 | 224 | 30.63 | Positive |
| A2 | 233 | 26.46 | Positive |
| A2 | 255 | 28.04 | Positive |
| A2 | 257 | 35.96 | Positive |
| A2 | 259 | 30.20 | Positive |
| TC Mean | | 30.26 | |
| SD | | 3.61 | |
| CV % | | 11.92 | |
| A3 | 210 | 28.83 | Positive |
| A3 | 220 | 30.82 | Positive |
| A3 | 245 | 32.31 | Positive |
| A3 | 251 | 36.04 | Positive |
| A3 | 260 | 28.90 | Positive |
| TC Mean | | 31.38 | |
| SD | | 2.98 | |
| CV % | | 9.50 | |
| Cont. | 203 | 26.73 | Positive |
| Cont. | 208 | 28.55 | Positive |
| TC Mean | | 27.64 | |
| SD | | 10.51 | |
| CV % | | 38.03 | |

Ref. FDV = Reference number of the animal

For comparison between vaccinated and non-vaccinated animals taking into account real-time RT-PCR results, the mean Ct from the control group were subtracted from the mean Ct from each of the different vaccinated groups. Miguel Angel Jiménez-Clavero et al. (2006). J Vet Diagn Invest 18:7-17) demonstrated that the detection achieved by the real-time RT-PCR assay showed a linear relationship between signal and the quantity of viral RNA present in the sample (equivalent $TCID_{50}$ infectious units per milliliter) on a log scale (correlation coefficient of 0.9948, and a slope of −3.334). For that reason, the Ct mean difference between each vaccinated group and the control group was divided by 3.334 and the log of the resultant number was calculated.

TABLE 10

Comparison between vaccinated and non-vaccinated animals according
to the real-time RT-PCR results at 3 days post-challenge (D + 3 p.i.)

| Group | Ct Mean/Group | SD | CV |
|---|---|---|---|
| A1 | 35.83 | 1.61 | 4.50 |
| A2 | 37.25 | 1.96 | 5.26 |
| A3 | 36.30 | 1.34 | 3.69 |
| Cont. | 35.98 | 18.86 | 52.43 |

| Ct differences | Ct differences | Ct dif/3.334 | log (Ct dif/3.334) |
|---|---|---|---|
| A1-Cont | −0.15 | −0.04 | 0.90 |
| A2-Cont | 1.27 | 0.38 | 2.40 |
| A3-Cont | 0.32 | 0.10 | 1.25 |

TABLE 11

Comparison between vaccinated and non-vaccinated animals according
to the real-time RT-PCR results at 5 days post-challenge (D + 5 p.i.)

| Group | Ct Mean/Group | SD | CV |
|---|---|---|---|
| A1 | 28.65 | 2.10 | 7.34 |
| A2 | 30.26 | 3.61 | 11.92 |
| A3 | 31.38 | 2.98 | 9.50 |
| Ct | 27.64 | 10.51 | 38.03 |

| Ct differences | Ct differences | Ct dif/3.334 | log (Ct dif/3.334) |
|---|---|---|---|
| A1-Cont | 1.01 | 0.30 | 2.01 |
| A2-Cont | 2.62 | 0.79 | 6.11 |
| A3-Cont | 3.74 | 1.12 | 13.24 |

Conclusions

The calculated numbers [log(Ct dif/3,334)] express the relationship between control and vaccinated groups. At 5 days post-challenge:

1. Animals vaccinated with $10^6 TCID_{50}$/dose had 2-fold less virus in blood than the control group (non-vaccinated animals)
2. Animals vaccinated with $10^{6.7} TCID_{50}$/dose had 6-fold less virus in blood than the control group (non-vaccinated animals)
3. Animals vaccinated with $10^7 TCID_{50}$/dose had 13-fold less virus in blood than the control group (non-vaccinated animals)

Example 4

Adjuvant and Dose Composition

Immunogenicity Experiment in 1-Month Old Lambs

Animals were vaccinated by subcutaneous route (2 mL) and revaccinated 3 weeks later.

Animals vaccinated with vaccines K1, K2, K6 and K8 were challenged 3-4 weeks after re-vaccination (challenge dose=$10^7$ $TCID_{50}$ of live virus/animal). Only animals vaccinated with vaccines K1 and K2 were protected.

TABLE 12

BTV PRE-IMMUNO VACCINES BATCH K COMPOSITION

| *Vaccine Batch | TCID$_{50}$ (2 mL dose) | ADJUVANT CONCENTRATION (2 mL dose) | LAMBS | SEPT 06 CHALLENGE |
|---|---|---|---|---|
| K1 | $3 \times 10^6$ | 4 mg Al$^{3+}$ 0.4 mg Quil-A | 7 | 7 |
| K2 | $1 \times 10^7$ | 4 mg Al$^{3+}$ 0.4 mg Quil-A | 10 | 5 |
| K3 | $3 \times 10^6$ | SP-Oil 5% | 7 | — |
| K4 | $1 \times 10^7$ | SP-Oil 5% | 10 | — |
| K5 | $3 \times 10^6$ | Montanide ™ ISA 206 50% | 7 | — |
| K6 | $1 \times 10^7$ | Montanide ™ ISA 206 50% | 10 | — |
| K7 | $3 \times 10^6$ | Montanide ™ ISA 207 50% | 7 | 7 |
| K8 | $1 \times 10^7$ | Montanide ™ ISA 207 50% | 10 | 5 |
| K9 | $1 \times 10^7$ | Drakeol 5- Arlacel 83V 60% | 10 | — |
| Non vaccinated | — | — | 12 | 5 |

*BTVi antigen: Complete culture, total inactivation process 72 h (10 mM BEI × 24 h + 5 mM BEI × 48 h)

Antibody Response after Vaccination

TABLE 13

*ELISA serological results

| Vaccine Batch | TCID$_{50}$ (2 mL dose) | ADJUVANT CONCENTRATION (2 mL dose) | LAMBS | ELISA D + 35 (2 WPRV) (% positives) |
|---|---|---|---|---|
| K1 | $3 \times 10^6$ | 4 mg Al$^{3+}$ 0.4 mg Quil-A | 7 | 86% (+1 doubtful) |
| K2 | $1 \times 10^7$ | 4 mg Al$^{3+}$ 0.4 mg Quil-A | 10 | 90% (+1 doubtful) |
| K3 | $3 \times 10^6$ | SP-Oil 5% | 7 | 14% (+1 doubtful) |
| K4 | $1 \times 10^7$ | SP-Oil 5% | 10 | 20% |
| K5 | $3 \times 10^6$ | Montanide ™ ISA 206 50% | 7 | 86% |
| K6 | $1 \times 10^7$ | Montanide ™ ISA 206 50% | 10 | 80% (+1 doubtful) |
| K7 | $3 \times 10^6$ | Montanide ™ ISA 207 50% | 7 | 56% (+2 doubtful) |
| K8 | $1 \times 10^7$ | Montanide ™ ISA 207 50% | 10 | 60% (+1 doubtful) |
| K9 | $1 \times 10^7$ | Drakeol 5- Arlacel 83V 60% | 10 | 20% (+3 doubtful) |
| Non vaccinated | — | — | 12 | 0% |

*Blocking ELISA using a VP7 specific Mab
WPRV = Weeks post-revaccination

TABLE 14

*Seroneutralization (SN) test results

| Vaccine Batch[1] | ADJUVANT/ 2 ml dose | LAMB | D + 42/45 3-4 WPRV 100% | 90% | Vaccine Batch[1] | ADJUVANT/ 2 mL dose | LAMB | D + 42/45 3-4 WPRV 100% | 90% |
|---|---|---|---|---|---|---|---|---|---|
| K1 $3 \times 10^6$ TCID$_{50}$/ 2 ml dose | 4 mg Al$^{3+}$ 0.4 mg Quil-A | 9 | *<2/2* | *4* | K2 $1 \times 10^7$ TCID$_{50}$/ 2 mL dose | 4 mg Al$^{3+}$ 0.4 mg Quil-A | 33 | 2 | 16 |
| | | 11 | *2* | *8* | | | 40 | <2 | 8 |
| | | 12 | <2 | 4 | | | 43 | <2 | 8 |
| | | 19 | <2 | 4 | | | 53 | *<2/2* | *8* |
| | | 22 | <2 | 8 | | | 59 | *<2* | *2* |
| | | 25 | <2 | 8 | | | 65 | 8 | 16 |
| | | 29 | *2* | *2* | | | 73 | *<2* | *4* |
| | | | | | | | 75 | <2-2 | 4 |
| | | | | | | | 79 | 2 | 4 |
| | | | | | | | 84 | *<2-2* | *8* |
| K7 $3 \times 10^6$ TCID$_{50}$/ 2 ml dose | Montanide ™ ISA 207 50% | 2 | <2 | *8-16* | K8 $1 \times 10^7$ TCID$_{50}$/ 2 ml dose | Montanide ™ ISA 207 50% | 34 | 4 | |
| | | 3 | <2 | <2 | | | 36 | 2 | |
| | | 5 | <2 | <2 | | | 52 | <2 | 2 |
| | | 6 | <2 | 2 | | | 54 | <2 | |
| | | 15 | <2 | <2 | | | 58 | <2 | 2 |
| | | 16 | <2 | <2 | | | 62 | 2 | |
| | | 18 | <2 | <2 | | | 63 | <2 | 4 |
| | | | | | | | 68 | <2 | <2 |
| | | | | | | | 76 | <2 | 2 |
| | | | | | | | 86 | <2 | |
| Control | — | 38 | <2 | <2 | | | | | |
| | | 41 | *<2* | *<2* | | | | | |
| | | 50 | <2 | <2 | | | | | |
| | | 51 | <2 | <2 | | | | | |
| | | 55 | *<2* | *<2* | | | | | |
| | | 60 | *<2* | *<2* | | | | | |
| | | 64 | <2 | <2 | | | | | |
| | | 77 | *<2* | *<2* | | | | | |
| | | 82 | <2 | <2 | | | | | |
| | | 88 | *<2* | *<2* | | | | | |
| | | 1 | <2 | <2 | | | | | |
| | | 90 | <2 | <2 | | | | | |

In bold and italics: Challenged animals bled at 45 days post-revaccination

*SN test: Based on the SN test in Vero cells described by the OIE with small modifications. The objective of the technique is to determine the highest sera dilution that is able to block the infection of 100 TCID$_{50}$ of BTV in Vero cells. Two lectures were done: considering a 100% of cytopathic effect reduction and a 90% of cytopathic effect reduction.

Challenge

According to ELISA results, vaccines formulated with SP-oil and Drakeol were not considered for a challenge. Based on safety results from previous experiments, vaccines formulated with Montanide™ ISA 206 were also discarded.

Lambs vaccinated with batches K1, K2, K7 and K8 were challenged at 24 days after re-vaccination. A group of 5 non-vaccinated controls were included.

TABLE 15

Challenge results

| Vaccine Batch | TCID$_{50}$ (2 mL dose) | ADJUVANT CONCENTRATION (2 mL dose) | NO. CHALLENGED ANIMALS | % ANIMALS SHOWING VIREMIA |
|---|---|---|---|---|
| K1 | $3 \times 10^6$ | 4 mg Al$^{3+}$ 0.4 mg Quil-A | 7 | *14% |
| K2 | $1 \times 10^7$ | 4 mg Al$^{3+}$ 0.4 mg Quil-A | 5 | 0% |
| K3 | $3 \times 10^6$ | SP-Oil 5% | — | — |
| K4 | $1 \times 10^7$ | SP-Oil 5% | — | — |
| K5 | $3 \times 10^6$ | Montanide ™ ISA 206 50% | — | — |
| K6 | $1 \times 10^7$ | Montanide ™ ISA 206 50% | — | — |
| K7 | $3 \times 10^6$ | Montanide ™ ISA 207 50% | 7 | 71% |
| K8 | $1 \times 10^7$ | Montanide ™ ISA 207 50% | 5 | 80% |
| K9 | $1 \times 10^7$ | Orakeol 5- Arlacel 83V 60% | — | — |
| Non vaccinated | — | — | 5 | 80% |

Bluetongue virus (BTV) was detected in blood samples by a real-time reverse transcription-polymerase chain reaction (RT-PCR)
*2 consecutive non conclusive results

Conclusions

The only vaccine able to prevent viremia was batch K2 formulated with $1 \times 10^7$ TCID$_{50}$/dose and Alhydrogel and Quil-A as adjuvant. Viremia was detectable in only 1 out of 5 animals vaccinated with batch K1 formulated with the same adjuvant but with a lower antigen concentration ($3 \times 10^6$ TCID$_{50}$/dose).

Results obtained with vaccines batches K7 and K8 formulated with Montanide™ ISA 206 (Seppic) were not satisfactory.

No challenge results are available for Montanide™ ISA 207 (Seppic) showing similar serological results.

Example 5

Final Vaccine Composition

TABLE 16

| Ingredients | Quantity/ml | Function | Reference to the standards |
|---|---|---|---|
| Active substances | | | |
| Inactivated and neutralized Bluetongue Virus (VLAi), minimum | $1.5 \times 10^6$ TCID$_{50}$ | Antigen | Internal monograph |
| Adjuvant components: | | | |
| Alhydrogel 2% | 192.6 mg (2 mg Al$^{3+}$) | Adjuvant | Internal monograph |

TABLE 16-continued

| Ingredients | Quantity/ml | Function | Reference to the standards |
|---|---|---|---|
| Quil-A | 200 µg | Adjuvant | Internal monograph |

TABLE 16-continued

| Ingredients | Quantity/ml | Function | Reference to the standards |
|---|---|---|---|
| Excipient components: | | | |
| Thiomersal | 0.1 mg | Preservative | Ph. Eur. Monograph n° 1625, Current edition |
| Saline solution | qs 1 ml | Diluent/ excipient | internal monograph |

What is claimed is:

1. A method of producing inactivated whole Bluetongue virus (BTV) that protects animals from viremia, the method comprising the steps of:
   a) treating the BTV with an inactivating agent using a 1:10 ratio of inactivating agent to BTV, while the BTV remains in a complete culture;
   b) homogenizing the inactivating agent/BTV mixture of step a) for at least 15 minutes;
   c) decanting the mixture of step b) into a container and agitating the mixture for about 24 hours;
   d) treating the agitated mixture resultant from step c) with an inactivating agent using a 1:20 ratio of inactivating agent to BTV therein;
   e) homogenizing the inactivating agent/BTV mixture of step d) for at least 15 minutes;
   f) decanting the mixture of step e) into a container and agitating the mixture for about 48 hours; and
   g) neutralizing the inactivating agent, and adjusting the final pH to about 7.2, if needed;

wherein the method results in inactivation of the BTV while maintaining the immunogenicity of the BTV.

2. The method of claim 1, wherein the inactivating agent is binary ethyleneimine (BEI).

3. The method of claim 1, wherein the final concentration of inactivating agent in step a) is about 10 mM.

4. The method of claim 1, wherein the final concentration of inactivating agent in step d) is about 5 mM.

5. The method of claim 1, wherein the whole Bluetongue virus is serotype 4.

* * * * *